US006956030B2

(12) United States Patent
Sequeira et al.

(10) Patent No.: US 6,956,030 B2
(45) Date of Patent: Oct. 18, 2005

(54) USE OF MOMETASONE FUROATE FOR TREATING UPPER AIRWAY DISEASES

(75) Inventors: Joel A. Sequeira, Scotch Plains, NJ (US); Francis M. Cuss, Basking Ridge, NJ (US); Keith B. Nolop, Millburn, NJ (US); Imtiaz A. Chaudry, North Caldwell, NJ (US); Nagamani Nagabhushan, Parsippany, NJ (US); James E. Patrick, Belle Meade, NJ (US); Mitchell Cayen, Bedminster, NJ (US)

(73) Assignee: Schering Corporation, Kenilworth, NJ (US)

(*) Notice: Subject to any disclaimer, the term of this patent is extended or adjusted under 35 U.S.C. 154(b) by 0 days.

(21) Appl. No.: 10/763,143

(22) Filed: Jan. 22, 2004

(65) Prior Publication Data

US 2004/0223920 A1 Nov. 11, 2004

Related U.S. Application Data

(63) Continuation of application No. 10/426,329, filed on Apr. 30, 2003, now Pat. No. 6,723,713, which is a continuation of application No. 10/053,204, filed on Jan. 16, 2002, now Pat. No. 6,677,323, which is a continuation of application No. 10/050,396, filed on Jan. 16, 2002, now Pat. No. 6,677,322, which is a continuation of application No. 09/535,208, filed on Mar. 27, 2000, now Pat. No. 6,365,581, which is a continuation of application No. 09/259,721, filed on Mar. 1, 1999, now Pat. No. 6,057,307, which is a continuation of application No. 08/911,300, filed on Aug. 14, 1997, now Pat. No. 5,889,015, which is a continuation of application No. 08/821,135, filed on Mar. 20, 1997, now Pat. No. 5,837,699, which is a continuation of application No. 08/701,536, filed on Aug. 22, 1996, now abandoned, which is a continuation of application No. 08/700,664, filed on Aug. 22, 1996, now abandoned, which is a continuation of application No. 08/444,582, filed on May 19, 1995, now abandoned, which is a continuation of application No. 08/376,506, filed on Jan. 23, 1995, now abandoned, which is a continuation-in-part of application No. 08/188,372, filed on Jan. 27, 1994, now abandoned.

(51) Int. Cl.[7] .................. A61K 31/56

(52) U.S. Cl. .................. 514/169; 514/172; 514/176; 514/182; 514/826; 514/958

(58) Field of Search .................. 514/169, 172, 514/176, 182, 826, 958

(56) References Cited

U.S. PATENT DOCUMENTS

| | | | |
|---|---|---|---|
| 4,472,393 A | 9/1984 | Shapiro | 424/243 |
| 6,127,353 A | 10/2000 | Yuen et al. | 514/172 |

FOREIGN PATENT DOCUMENTS

| | | |
|---|---|---|
| CA | 2062854 | 9/1992 |
| EP | 0 518 600 A1 | 12/1992 |
| EP | 0 518 601 A1 | 12/1992 |
| WO | WO 92/04365 | 3/1992 |
| WO | WO 92/06706 | 4/1992 |

OTHER PUBLICATIONS

H. A. Orgel et al., "Clinical, Rhinomanometric, and Cytologic Evaluation of Seasonal Allergic Rhinitis Treated with Beclomethasone Dipropionate as Aqueous Nasal Spray or Pressurized Aerosol," *Journal of Allergy and Clinical Immunology*, vol. 77, pp. 858–864, 1986.

PR Newswire, Nov. 30, 1988, 4 pages.

(Continued)

*Primary Examiner*—S. Mark Clardy
(74) *Attorney, Agent, or Firm*—Robert A. Franks; Geraldine F. Baldwin; Robert J. Lipka

(57) ABSTRACT

The administration of aerosolize particles of mometasone furoate in the form of dry powders, solutions, or aqueous suspension for treating corticosteroid-responsive diseases of the surfaces of upper and/or lower airway passages and/or lungs, e.g., allergic rhinitis and asthma is disclosed.

9 Claims, 1 Drawing Sheet

OTHER PUBLICATIONS

J. M. Swinehart et al., "Mometasone Furoate Lotion Once Daily Versus Triamcinolone Acetonide Lotion Twice Daily in Psoriasis," *International Journal of Dermatology*, vol. 28, pp. 680–681, 1989.

H. J. Lee et al., "Anti–Inflammatory Steroids: Research Trends and New Compounds," *Drugs of Today*, vol. 25, pp. 577–588, 1989.

P. Viglioglia et al., "Once–Daily 0.1% Mometasone Furoate Cream Versus Twice–Daily 0.1% Betamethasone Valerate Cream in the Treatment of a Variety of Dermatoses," *The Journal of International Medical Research*, vol. 18, pp. 460–467, 1990.

Business Wire, Nov. 14, 1990, 5 pages.

J. W. Kelly et al., "Safety and Efficacy of Mometasone Furoate Cream in the Treatment of Steroid Responsive Dermatoses," *Australasian Journal of Dermatology*, vol. 32, pp. 85–91, 1991.

S. Lidén, "Optimal Efficacy of Topical Corticoids in Psoriasis," *Seminars in Dermatology*, vol. 11, pp. 275–277, 1992.

Predicasts Marketletter, Mar. 30, 1992, 3 pages.

I. M. Richards et al., "Novel Steroid–Based Inhibitors of Lung Inflammation," *Clinical and Experimental Allergy*, vol. 22, pp. 432–439, 1992.

C. J. Wang et al., "A Sensitive Enzyme Immunoassay (EIA) for Quantitation of Mometasone Furoate (SCH 32088) Directly in Biological Fluids," Abstract 2119, *FASEB J.*, vol. 6, No. 4, p. A1302, 1992.

C–J. Wang et al., "A Competitive Enzyme Immunoassay for the Direct Determination of Mometasone Furoate (SCH 32088) in Human Plasma," *Journal of Pharmaceutical and Biomedical Analysis*, vol. 10, pp. 473–479, 1992.

H. Degreef et al., "The New Corticosteroids: Are They Effective and Safe?" *Dermatologic Clinics*, vol. 11, pp. 155–160, 1993.

D. Debrovner, "Why Asthmatics Need You," *American Druggist*, pp. 24–27, Aug. 1994.

M. Drouin et al., "Once Daily Mometasone Furoate Aqueous Nasal Spray is as Effective as Twice Daily Beclomethasone Dipropionate for Treating Perennial Allergic Rhinitis Patients," *Annals of Allergy, Asthma & Immunology*, vol. 77, pp. 153–160, 1996.

US 6,956,030 B2

USE OF MOMETASONE FUROATE FOR TREATING UPPER AIRWAY DISEASES

CROSS-REFERENCE TO RELATED APPLICATIONS

This application is a continuation of application Ser. No. 10/426,329, filed Apr. 30, 2003, now U.S. Pat. No. 6,723,713, which is a continuation of application Ser. No. 10/050,396 (now U.S. Pat. No. 6,677,322) and U.S. Ser. No. 10/053,204 (now U.S. Pat. No. 6,677,323), both of which were filed Jan. 16, 2002 as continuations of application Ser. No. 09/535,208 filed Mar. 27, 2000 (now U.S. Pat. No. 6,365,581), which is a continuation of application Ser. No. 09/259,721 filed Mar. 1, 1999 (now U.S. Pat. No. 6,057,307), which is a continuation of application Ser. No. 08/911,300 filed Aug. 14, 1997 (now U.S. Pat. No. 5,889,015), which is a continuation of application Ser. No. 08/821,135 filed Mar. 20, 1997 (now U.S. Pat. No. 5,837,699) and U.S. Ser. No. 08/700,664 filed Aug. 22, 1996 (now abandoned), said application Ser. No. 08/700,664 being a continuation of application Ser. No. 08/444,582 filed May 19, 1995 (now abandoned) and said application Ser. No. 08/821,135 being a continuation of application Ser. No. 08/701,536 filed Aug. 22, 1996 (now abandoned), each of said application Ser. Nos. 08/444,582 and 08/701,536 being a continuation of application Ser. No. 08/376,506 filed Jan. 23, 1995 (now abandoned), which itself is a continuation-in-part of application Ser. No. 08/188,372 filed Jan. 27, 1994 (now abandoned).

INTRODUCTION TO THE INVENTION

This invention relates to the treating of corticosteroid-responsive diseases of the upper and lower airway passages and lungs, such as asthma, by orally or intranasally administering to said passages and lungs an amount of mometasone furoate effective for treating such diseases while minimizing systemic absorption and side effects associated with such systemic absorption.

Mometasone furoate is a corticosteroid approved for topical dermatologic use to treat inflammatory and/or pruritic manifestations of corticosteroid-responsive dermatoses. The compound may be prepared in accordance with the procedures disclosed in U.S. Pat. Nos. 4,472,393, 4,731,447, and 4,873,335, which U.S. Patents are hereby incorporated by reference.

Certain corticosteroids, e.g., beclomethasone dipropionate are commercially available for the treatment of diseases of airway passages and lungs such as rhinitis and bronchial asthma. However, the art teaches that not every corticosteroid having topical anti-inflammatory activity is active in treating rhinitis and/or asthma. Furthermore, even though a topically active corticosteroid may exhibit activity in treating bronchial asthma, the long term use of such steroids has been limited by the occurrence of serious systemic side-effects, including hypothalamic-pituitary-adrenal (HPA) axis suppression. The introduction of topically active steriods administered by metered-dose inhalation has greatly reduced but not eliminated the detrimental system side-effects of steroid therapy in the treatment of asthma. Unfortunately, however, a large portion of an inhaled corticosteriod dose is swallowed by the patient. Since certain corticosteroids are readily bioavailable, the swallowed portion of the dose may reach the systemic circulation through the gastrointestinal tract and may cause unwanted systemic side-effects. Some corticosteroids currently approved for treating asthma have systemic bioavailability after oral ingestion of greater than 10% (budesonide) or even 20% (triamcinolone acetonide and flunisolide) of the inhalation dose. Thus, a topically active steroid which is not readily bioavailable would provide a therapeutic advantage over other topically active corticosteroids that are more systematically bioavailable and it would also be superior to any corticosteroid orally administered by the oral swallowing of, for example, a solution, tablet or capsule.

Discovering an effective corticosteroid for treating diseases such as asthma with low systemic side-effects is unpredictable. For example, the corticosteroid tipredane exhibited not only good initial anti-inflammatory activity against asthma but also low systemic side effects. However, development of tipredane for treating asthma has been discontinued because clinical trials have not demonstrated a level of efficacy in treating asthma which would be considered therapeutically useful. It has recently been disclosed that butixocort propionate, another potent topical anti-inflammatory corticosteroid having reportedly low systemic side-effects is under development (Phase II) for treating chronic bronchial asthma. While the clinical results currently available from the Phase II studies show butixocort propionate has some efficacy, it remains to be seen if the efficacy in treating asthma will be sufficient to justify continuing the clinical development.

Thus, it would be desirable to find a corticosteroid which is therapeutically effective in treating disease of the airway passages and lungs such as asthma and which also exhibits low bioavailability and low systemic side-effects when it is administered intra-nasally or by oral inhalation.

SUMMARY OF THE INVENTION

The present invention provides a method of treating a corticosteroid-responsive disease of the upper or lower airway passages and/or of the lungs in patients afflicted with said disease, which comprises administering once-a-day to said passages or lungs of said patients a substantially non-systematically bio-available amount of aerosolized particles of mometasone furoate effective for treating said disease.

In a preferred aspect of the present invention, there is provided a method of treating allergic or non-allergic rhinitis in patients afflicted with said rhinitis which comprises administering once-a-day to the surfaces of the upper airway passages of said patients an amount of aerosolized particles of mometasone furoate effective to maximize treating said rhinitis in the upper airway passages while simultaneously substantially minimizing systemic absorption thereof.

In another preferred aspect of the present invention, there is provided a method of treating allergic and/or inflammatory diseases of the lower airway passages and/or lungs in patients afflicted with at least one of said diseases which comprises administering once-a-day via oral inhalation to the surfaces of the upper and lower airway passages of said patients an amount of aerosolized particles of mometasone furoate effective to maximize topically treating said allergic and/or inflammatory disease in the lower airway passage and/or lungs while simultaneously substantially minimizing the systemic absorption thereof.

The present invention also provides a method of producing a rapid onset of action in treating asthma in a patient afflicted with asthma which comprises administering via oral inhalation to the surfaces of the lower airway passages and lungs of the patient an amount of aerosolized particles of mometasone furoate effective to produce a rapid onset of action in treating asthma while simultaneously substantially minimizing systemic absorption thereof.

DETAILED DESCRIPTION OF THE INVENTION AND OF THE PREFERRED EMBODIMENTS

Figure 1:
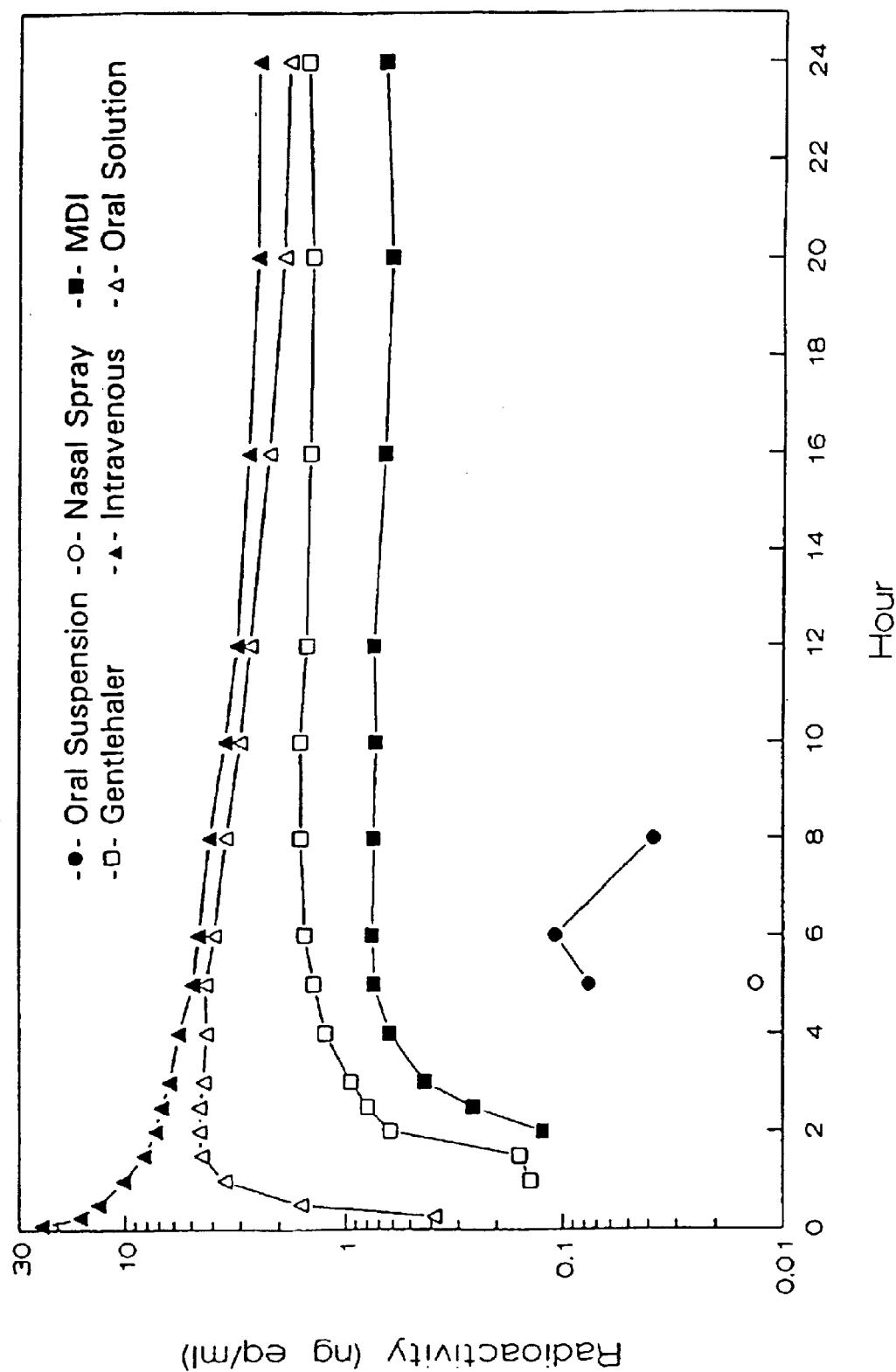
FIG. 1 graphically illustrates the variation with time (measured in hours) of the plasma concentrations of total radioactivity (measured in ng-eq/mL) following administration of tritium-labelled mometasone furoate by various formulations and routes of administration to male volunteers. The curve plotted with the darkened circles (●) represents the variations of plasma concentrations with time after administration of radio-labelled drug by oral suspension; the curve plotted with open circles (○) represents the variation of plasma concentrations with time after administration of drug by nasal spray; the curve plotted with the darkened squares (■) represents the variation of plasma concentrations with time after administration by a metered dose inhaler; the curve plotted with the open squares (□) represent the variation of plasma concentrations with time after administration of drug by Gentlehaler; the curve plotted with the darkened triangles (▼) represents the variation of plasma concentrations with time after administration of drug by the intravenous route and the curve plotted with the open triangles (Δ) represent the variations of plasma concentration with time after administration of the radio-labelled drug via oral solution. See Tables in Results section hereinafter.

Although corticosteroids have been effective in treating airway passage diseases such as asthma, such treating with corticosteroids may often cause systemic side-effects such as suppression of hypothalamic-pituitary-adrenocortical ("HPA") axis function by reducing corticotrophin (ACTH) production, which in turn leads to a reduced cortisol secretion by the adrenal gland.

We have surprisingly discovered that mometasone furoate exhibits superior anti-inflammatory effects in treating airway passage diseases such as asthma and allergic rhinitis by acting on surfaces of the upper and lower airways passages and lungs while having a substantially minimum systemic effect. The substantial minimization of the systemic effect of mometasone furoate administered intranasally or by oral inhalation has been measured by High Performance Liquid Chromatography (HPLC) metabolite profiling of plasma radioactivity of mometasone furoate, its substantially complete (>98%) first-pass metabolism in the liver and by a minimal reduction in cortisol secretion levels.

When mometasone furoate is administered orally (i.e., swallowed as an oral suspension) or by oral or nasal inhalation, there is a substantial absence of absorption systemically into the bloodstream of mometasone furoate i.e., there is essentially no parent drug (substantially less than 1% of mometasone furoate) which reaches the bloodstream from the gastrointestinal tract. Any mometasone furoate found in the bloodstream after it has been administered by oral or nasal inhalation has already passed through the lungs and/or airway passage tissue. Therefore, there is no "wasted" drug (i.e., drug that reaches the relevant tissue in the lungs and/or airways only via the bloodstream). Thus, mometasone furoate is an ideal drug for treating diseases of the airway passages and lungs such as asthma and allergic rhinitis.

Administering mometasone furoate to the surfaces of the airways of asthmatic patients will maximize the therapeutic index. The term "therapeutic index", as used herein, means the ratio of local efficacy to systemic safety. The local efficacy in asthma of corticosteroids such as mometasone furoate is assessed by measurement of lung function and reduction in frequency and severity of symptoms. Systemic safety of such cortisteroids is usually measured by HPA-axis function; other measures of systemic effect include, for example, growth suppression, bone density, and skin thickness measurements.

In addition to the superb safety profile exhibited by mometasone furoate administered to patients with asthma and allergic rhinitis in accordance with the present invention, mometasone furoate also exhibits an unexpected higher level of efficacy in treating asthma and allergic rhinitis than the superb safety profile would suggest.

The term "rapid onset of action in treating asthma in patients afflicted with asthma" as used herein means that there is a significant clinically meaningful improvement in the pulmonary function of asthma patients within 7, 3 and even 1 day(s) of the initial administration of mometasone furoate in accordance with the present invention. These unexpected results were obtained in a placebo-controlled, parallel group Phase I study of safety and pilot efficacy wherein mometasone furoate was administered by a metered dose inhaler twice daily to forty-eight patients with mild asthma (12 patients in each treatment group). The three groups of patients treated with mometasone furoate exhibited clinically meaningful increases in pulmonary function as measured by improvements in the forced expiratory volume in one second ($FEV_1$).

These increases in $FEV_1$ are unexpectedly superior even though mometasone furoate exhibits a superb safety profile. Furthermore, one would not predict the increases based on the known clinical data for other corticosteroids available for treating asthma.

The term "corticosteroid-responsive disease of the airway passage ways and lungs" as used herein means those allergic, non-allergic and/or inflammatory diseases of the upper or lower airway passages or of the lungs which are treatable by administering corticosteroids such as mometasone furoate. Typical corticosteroid-responsive diseases include asthma, allergic and non-allergic rhinitis as well as non-malignant proliferative and inflammatory diseases of the airways passages and lungs.

The term "asthma" as used herein includes any asthmatic condition marked by recurrent attacks of paroxysmal dyspnea (i.e., "reversible obstructive airway passage disease") with wheezing due to spasmodic contraction of the bronchi (so called "bronchospasm"). Asthmatic conditions which may be treated or even prevented in accordance with this invention include allergic asthma and bronchial allergy characterized by manifestations in sensitized persons provoked by a variety of factors including exercise, especially vigorous exercise ("exercise-induced bronchospasm"), irritant particles (pollen, dust, cotton, cat dander) as well as mild to moderate asthma, chronic asthma, severe chronic asthma, severe and unstable asthma, nocturnal asthma, and psychologic stresses. The methods of this invention are particularly useful in preventing the onset of asthma in mammals e.g., humans afflicted with reversible obstructive disease of the lower airway passages and lungs as well as exercise-induced bronchospasm.

The methods of this invention are also useful in treating allergic and non-allergic rhinitis as well as non-malignant proliferative and/or inflammatory disease of the airway passages and lungs.

The term "allergic rhinitis" as used herein means any allergic reaction of the nasal mucosa and includes hay fever (seasonal allergic rhinitis) and perennial rhinitis (non-seasonal allergic rhinitis) which are characterized by seasonal or perennial sneezing, rhinorrhea, nasal congestion, pruritis and eye itching, redness and tearing.

The term "non-allergic rhinitis" as used herein means eosinophilic nonallergic rhinitis which is found in patients with negative skin tests and those who have numerous eosinophils in their nasal secretions.

The term "non-malignant prolifertive and/or inflammatory disease" as used herein in reference to the pulmonary system means one or more of (1) alveolitis, such as extrinsic allergic alveolitis, and drug toxicity such as caused by, e.g. cytotoxic and/or alkylating agents; (2) vasculitis such as Wegener's granulomatosis, allergic granulomatosis, pulmonary hemangiomatosis and idiopathic pulmonary fibrosis, chronic eosinophilic pneumonia, eosinophilic granuloma and sarcoidoses.

The mometasone furoate administered, for example, by oral inhalation or intranasally to treat disease of the lower and/or upper airway passages and/or lungs may be used as monotherapy or as adjuvant therapy with for example cromolyn sodium or nedocromil sodium (available from Fisons); immunosuppressive agents such as methotrexate sodium (available from Astra Pharmaceutical Products, Inc.), oral gold, or cyclosporine A (available from Sandoz under the SANDIMMUNE® tradename); bronchodilators such as albuterol (available from Schering Corporation under the PROVENTIL® tradename) or theophylline (available from Key Pharmaceuticals of Schering Corporation under the Theo-Dur® tradename).

The devices found useful for providing measured substantially non-systematically bioavailable amounts of aerosolized mometasone furoate or aerosolized pharmaceutical compositions thereof for delivery to the oral airway passages and lungs by oral inhalation or intranasally by inhalation include pressurized metered-dose inhalers ("MDI") which deliver aerosolized particles suspended in chlorofluorocarbon propellants such as CFC-11, CFC-12, or the non-chlorofluorocarbons or alternate propellants such as the fluorocarbons, HFC-134A or HFC-227 with or without surfactants and suitable bridging agents; dry-powder inhalers either breath activated or delivered by air or gas pressure such as the dry-powder inhaler disclosed in the Schering Corporation International Patent Application No. PCT/US92/05225, published 7 Jan. 1993 as well as the TURBUHALER™ (available from Astra Pharmaceutical Products, Inc.) or the ROTAHALER™ (available from Allen & Hanburys) which may be used to deliver the aerosolized mometasone furoate as a finely milled powder in large aggregates either alone or in combination with some pharmaceutically acceptable carrier e.g. lactose; and nebulizers. The inhalation of aerosolized drugs by use of nebulizers and metered-dose inhalers such as used to deliver VANCENASE® (brand of beclomethasone dipropionate) inhalation aerosol (available from Schering Corporation, Kenilworth, N.J.) is disclosed in Remington's Pharmaceutical Sciences, Mack Publishing Co. Easton Pa., 15th Ed. Chapter 99, pages 1910–1912.

Mometasone furoate may be also administered in specific, measured amounts in the form of an aqueous suspension by use of a pump spray bottle such as the bottles used to deliver VANCENASE AQ® Nasal Spray as well as the spray bottle disclosed in the Schering Corporation Industrial Design Deposit DM/026304, registered by the Hague Union on Jun. 1, 1993 (each are available from Schering Corporation). The aqueous suspension compositions of the present invention may be prepared by admixing mometasone furoate or mometasone furoate monohydrate (preferably mometasone furoate monohydrate) with water and other pharmaceutically acceptable excipients. See International Application No. PCT/US91/06249 especially Examples 1–5 for preparation of mometasone furoate monohydrate and aqueous suspensions containing same. The aqueous suspensions of the invention may contain from about 0.01 to 10.0 mg, preferably 0.1 to 10.0 mg of mometasone furoate monohydrate per gram of suspension. The aqueous suspension compositions according to the present invention may contain, inter alia, water, auxiliaries and/or one or more of the excipients, such as: suspending agents, e.g., microcrystalline cellulose, sodium carboxymethylcellulose, hydroxpropyl-methyl cellulose; humectants, e.g. glycerin and propylene glycol; acids, bases or buffer substances for adjusting the pH, e.g., citric acid, sodium citrate, phosphoric acid, sodium phospate as well as mixtures of citrate and phosphate buffers; surfactants, e.g. Polysorbate 80; and antimicrobial preservatives, e.g., benzalkonium chloride, phenylethyl alcohol and potassium sorbate.

Based on the judgment of the attending clinician, the amount of mometasone furoate administered and the treatment regimen used will, of course, be dependent on the age, sex and medical history of the patient being treated, the severity of the specific asthmatic or non-malignant pulmonary disease condition and the tolerance of patient to the treatment regimen as evidenced by local toxicity (e.g., nasal irritation and/or bleeding) and by systemic side-effects (e.g. cortisol level). Cortisol (also referred to as hydrocortisone) is the major natural glucocorticosteroid elaborated by the adrenal cortex.

For the treatment of allergic, non-allergic rhinitis and/or inflammatory diseases of the upper or lower airway passages to treat for example asthma or allergic or non-allergic rhinitis, the substantially non-systematically bioavailable amount of mometasone furoate which may be administered as an aqueous suspension or dry powder is in the range of about 10 to 5000 micrograms ("mcg")/day, 10 to 4000 mcg/day, 10 to 2000 mcg/day, 25–1000 mcg/day, 25 to 400 mcg/day, 25–200 mcg/day, 25–100 mcg/day or 25–50 mcg/day in single or divided doses.

In treating allergic and non-allergic rhinitis, the aqueous suspension of mometasone furoate may be administered intranasally by inserting an appropriate device (such as the pump spray bottle used to deliver Vancenase AQ® Nasal Spray as well as the spray bottle disclosed in the Schering Corporation Industrial Design Deposit DM/026304 registered Jun. 1, 1993) into each nostril. Active drug is then expelled (nasal spray device) or could be nasally inhaled (sniffed) as a powder. Efficacy is generally assessed in a double blind fashion by a reduction in nasal symptoms (e.g., sneezing, itching, congestion, and discharge). Other objective measurements (e.g., nasal peak flow and resistance) can be used as supportive indices of efficacy.

For treatment of allergic and/or inflammatory diseases of the lower airways and lung parenchyma especially diseases such as asthma, chronic obstructive pulmonary disease ("COPD"), granulomatus diseases of the lungs and lower airway passage, non-malignant proliferative disease of the lungs e.g., idiopathic pulmonary fibrosis, hypersensitivity pneumonitis and bronchopulmonary dysplasia the following dosage ranges of mometasone furoate may be used: (1) for metered dose inhalers with standard CFC or alternate propellant about 10 to 5000 mcg/day or 10 to 4000 mcg/day or 10 to 2000 mcg/day, or 50 to 1000 mcg/day or 25 to 100 mcg/day, or 25 to 400 mcg/day, or 25 to 200 mcg/day, or 25–50 mcg/day; the preferred dosage range is 50 to 1000 micrograms a day and the preferred dosages are 25, 100, 200 and 250 mcg, administered in one to four puffs; preferably one to three puffs, once-a-day; (2) for the dry powder inhaler—about 10 to 5000 mcg/day or 10–4000 mcg/day or 10–2000 mcg/day or 25–1000 mcg/day or 25–400 mcg/day or 25–200 mcg/day or 50–200 mcg/day or 25–50 mcg/day of anhydrous mometasone furoate; the preferred dosage range of anhydrous mometasone furoate in the dry powder inhaler is 50 to 600 micrograms a day more preferably 100 to 600 mcg a day and the preferred dosages are 50, 100, 200 and 250 mcg, administered in one to three puffs, once-a-day; typically the metered dose inhaler unit will contain 120 doses; (3) for aqueous suspension for inhalation, the preferral dosage ranged from 25 to 800 mcg/100 $\mu$L and the dosages are 25, 50, 100, 125, 150, 175, 200, 225, 250, 300, 400, 500 and 800 mcg/100 $\mu$L of mometasone furoate in single or divided doses. The aqueous suspension of mometasone furoate has been found to be safe and effective in treating allergic rhinitis e.g. seasonal allergic rhinitis from 25 micrograms up to 1600 micrograms administered once-a-day; the preferred dosage range is 25–800 micrograms a day, although no improvement in treatment is typically found above 400 micrograms a day. The most preferred dosages are 25, 50 and 100 micrograms administered twice to each nostril, once-a-day for a total once-a-day dose of 100, 200 and 400 mcg. Typically 2–4 mL of the aqueous suspension of mometasone furoate monohydrate may be placed in a plastic nebulizer container and the patient would inhale for 2–10 minutes. The total dosage placed in such a container would be in the range of 300–3000 mcg.

In a preferred aspect of this invention, the anhydrous mometasone furoate may be admixed with a dry excipient, for example dry lactose for use in the dry powder inhaler. The mometasone furoate:dry lactose ratio varies broadly from 1:19 to 1:0, and preferably it is 1:19 to 1:4. Typically, the suitable anhydrous mometasone furoate dosage range is 25 to 600 micrograms administered once-a-day. The preferred mometasone furoate dosages for admixture with dry lactose are 25, 100, 200 and 250 micrograms which are administered in one to three puffs a day. The preferred combined mometasone furoate:lactose dose is 500 micrograms for each dose. For example, for the preferred 1:19 ratio, 25 micrograms of anhydrous mometasone furoate are admixed with 475 micrograms of anhydrous lactose and for the preferred 1:4 ratio, 100 micrograms of anhydrous mometasone furoate are admixed with 400 micrograms of anhydrous lactose, to produce the 500 microgram dose of the mometasone furoate:lactose admixture.

The dosing regimen for lower airway diseases such as asthma will vary from four times a day to twice a day to once-a-day. Once-a-day (such as at 8 a.m.) maintenance therapy should be adequate, once control of asthma is achieved. It is anticipated, however, that the superior therapeutic index of mometasone furoate will result in effective treatment of patients by once-a-day dosing even at the initiation of the methods of this invention.

For other diseases of the lower airway passages and/or lungs, dosing is likely to be two to four times daily, preferably two to three times and most preferably once daily, when adequate control of the disease is achieved.

For any route of administration, divided or single doses may be used. For example, when a metered dose inhaler is used to deliver, for example, 500 mcg of aerosolized mometasone furoate, once-a-day, two puffs of 250 mcg would normally be used to deliver the aerosolized drug. When a plastic nebulizer container is used to deliver for example 200 micrograms a day of an aqueous suspension of mometasone furoate, two squeezes of 50 micrograms into each nostril would normally be used to deliver the drug. When the metered dose inhaler is used to deliver for example 200 mcg of anhydrous mometasone furoate, two puffs of 500 micrograms of an admixture of 100 mcg of mometasone furoate and 400 mcg of lactose once-a-day would normally be used to deliver the aerosolized drug.

The effectiveness of the methods of this invention can also be shown clinically in mammals, e.g. humans being afflicted with or susceptible to a non-malignant proliferative and/or inflammatory disease such as idophathic pulmonary fibrosis or using patients with inter alia the following entry criteria: 1. an improved Karnofsky performance status; (2) adequate pulmonary function for undergoing the required inhalation treatment satisfactorily as evidenced by (a) an improved forced expiratory volume (FEV) and (b) an improved forced vital capacity (FVC) and (3) no serious systemic infections and/or fever.

Similar results to those achieved in treating asthma are expected.

Results

The following is a summary of the clinical results obtained in treating asthma and asthmatic conditions.

Prior to enrollment, all patients are thoroughly evaluated via a medical history, physical examination, chest x-ray, an electrocardiogram and hematologic and blood chemistry measurements. Pulmonary function including peak expiatory flow rate (PEF), forced expiratory volume in one second ($FEV_1$), and forced vial capacity (FVC) and cortisol levels may be also measured. Subjective and objective symptoms including the number and severity of coughing bouts, shortness of breath, chest tightness and wheezing are normally assessed.

Several Phase I studies were conducted using mometasone furoate formulated for delivery as a suspension in a pressurized metered dose inhaler (MDI). In a randomized, third-party blinded, placebo-controlled rising single-dose safety and tolerance study, aerosolized mometasone furoate was administered by a metered dose inhaler to eight healthy male volunteers. Doses were administered at 11 p.m. and plasma cortisol concentrations were measured during the following 24-hour period. Compared to placebo, mometasone furoate doses of 1000 mcg, 2000 mcg and 4000 mcg reduced the 24-hour area under the curve plasma cortisol profile (AUC 0–24) by 13%, 23% and 36%, respectively. Equivalent doses of beclomethasone dipropionate (BDP) reduced the AUC 0–24 by 30%, 38% and 65%, respectively.

In a subsequent placebo-controlled, parallel group Phase I study of safety and pilot efficacy, mometasone furoate was given by MDI at dose of 500 mcg twice daily ("BID"), 1 mg BID, and 2 mg BID for 28 days to 48 patients with mild asthma (12 patients per treatment group) or placebo also given BID by MDI. Therapy with mometasone furoate was well tolerated, and all patients completed the therapy. Patients treated with 1000 mcg of mometasone furoate daily had values for 8 a.m. plasma cortisol that were similar to those of patients treated with 2000 mcg of mometasone furoate daily at all time points; there were small decreases from Baseline on Days 15 and 21 which were statistically significant compared to placebo. Patients treated with 4000 mcg of mometasone furoate daily had greater decreases in plasma cortisol, which were statistically different from placebo from Day 3 through Day 28. The mean values of urinary cortisol tended to decrease during the course of the study for the 2000 mcg and 4000 mcg groups; the mean values of urinary cortisol for the 1000 mcg group were not different from placebo. With respect to the responses to ACTH infusions at post-treatment (Day 30), all of the treatment groups demonstrated significant increases from Baseline in plasma cortisol both immediately after the 8 hour infusion and 24 hours after the beginning of the infusion (i.e., a normal response). The asthma patients treated with mometasone furoate in this placebo-controlled Phase I study exhibited unexpected, clinically meaningful increases in $FEV_1$ values that were ≧15% from Baseline at a majority of time points. The mean increases in $FEV_1$ values for the 1 mg/day, 2 mg/day and 4 mg/day treatment groups were statistically significantly greater than for the placebo group at every time point from day 3 to day 28. The 1 mg/day treatment group showed a statistically significant, clinically meaningful improvement in the $FEV_1$ value even on day 1 compared to the $FEV_1$ value for the placebo group.

In a recently completed, randomized, double-blinded multicenter, Phase II study, 395 patients with asthma requiring treatment with inhaled corticosteroids were randomized to one of the five treatment groups: mometasone furoate (MDI 112 mcg/day, 400 mcg/day or 1000 mcg/day, beclomethasone dipropionate (BDP) 336 mcg/day, or placebo. All treatment regimens consisted of BID dosing for 4 weeks. PROVENTIL inhalation aerosol (albuterol, USP) was supplied as rescue medication.

Evaluation of Efficacy

Efficacy was evaluated by spirometry and by physician and patient evaluation of asthma signs and symptoms. The forced expiratory volume in one second ($FEV_1$), forced vital capacity (FVC), and forced expiratory flow between 25% to 75% ($FEF_{25\%-75\%}$) were measured at each visit by the investigator. The peak expiratory flow rate (PEFR) was measured twice daily (AM and PM) by the patient. $FEV_1$ at endpoint of treatment (last evaluable visit) was the primary measure of efficacy. The investigator (at all visits) and the patient (twice daily) rated wheezing, tightness in chest, shortness of breath, and cough on a scale from 0 (None) to 6 (Incapacitating). In addition, the investigator rated the overall condition of asthma on the same scale at each visit, and the patient kept a diary of the total number of asthma attacks each day, the number of night awakenings due to asthma, and the total number of puffs of Proventil (protocol-permitted rescue medication) used. The actual value and changes from Baseline were analyzed for each visit.

All treatments were well tolerated; most frequently reported adverse events were dysphonia, pharyngitis, cough and headache, which were generally mild to moderate in severity. All 4 active treatments were statistically superior to placebo at all visits with respect to improvement in $FEV_1$ ($p<0.01$) compared with the placebo treatment group which experienced a mean decrease in this variable. The two higher doses of mometasone furoate were superior to beclomethasone dipropionate (BDP) at Days 14, 21 and 28. At Day 21 and Day 28, the two higher doses of mometasone furoate were significantly superior to the low mometasone furoate dose. Diary a.m. and p.m. PEFR data were similar to $FEV_1$. During the final week of treatment, all mometasone furoate doses were significantly better than 336 mg dose of BDP in improving a.m. PEFR. Total asthma scores, assessment of overall condition, and therapeutic response to treatment confirmed superiority of all mometasone furoate doses relative to placebo, as well as relationships among the active treatment groups.

Mometasone furoate (intranasally in the form of an aqueous suspension of mometasone furoate monohydrate) has been used for treating patients with seasonal allergic rhinitis. The term "seasonal allergic rhinitis" as used herein means a hypersensitivity response to seasonal pollens characterized by inflammation of the nasal mucous membranes, nasal discharge, sneezing and congestion.

Several Phase I studies have been completed using the aqueous nasal spray suspension formulation of mometasone furoate monohydrate. In a randomized, third party-blinded, placebo-controlled rising single-dose safety and tolerance study, the aqueous nasal spray suspension formulation was administered to eight healthy male volunteers. Doses were administered at 11 pm, and plasma cortisol concentrations were measured during the following 24-hour period. Compared to placebo, mometasone furoate at doses of 1000 mcg, 2000 mcg, and 4000 mcg did not significantly affect the 24-hour area under the curve plasma cortisol profile (AUC 0–24).

In a follow-up multiple dose study, 48 normal male volunteers were empaneled in a randomized, third party-blinded, placebo and active-controlled parallel group study. Twelve volunteers in each of four groups received one of the following treatments for 28 days: A) Intranasal aqueous nasal spray suspension formulation of mometasone furoate monohydrate, 400 mcg/day; B) Intranasal aqueous nasal spray suspension formulation of mometasone furoate monohydrate, 1600 mcg/day; C) Intranasal placebo; D) Oral prednisone, 10 mg/day. All treatments were administered as once daily dosing in the morning. The mometasone furoate aqueous nasal spray formulation was well tolerated, and all patients completed the study. Neither of the 2 doses of the mometasone furoate aqueous nasal spray formulation were associated with any changes in cortisol secretion compared to placebo.

In addition, a single-dose absorption, excretion and metabolism study using 200 mcg of $^3H$-mometasone furoate as the nasal spray formulation was conducted in 6 normal male volunteers. When systemic absorption (based on urinary excretion) was compared to an intravenously administered dose of $^3H$-mometasone furoate, it was 8%. The plasma concentrations of parent drug could not be determined by metabolite profiling because the levels of plasma radioactivity were below the limit of quantification. These data are consistent with substantially less than 1% of bioavailability of mometasone furoate. See Tables 1 to 2 herein below.

In a dose ranging safety and efficacy study, the mometasone furoate aqueous nasal spray formulation at doses of 50 mcg/day, 100 mcg/day, 200 mcg/day, 800 mcg/day or placebo was administered to 480 patients with seasonal allergic rhinitis for 4 weeks. All treatments were well tolerated; results of statistical analysis indicated that all doses of mometasone furoate were effective relative to placebo. These results showed that administration of an aqueous suspension of mometasone furoate as a nasal spray to patients with seasonal allergic rhinitis was effacious, well tolerated with little potential for systemic side effects and are consistent with the low oral bioavailability of mometasone furoate.

The term "rapid onset of action in treating allergic or seasonal allergic rhinitis" as used herein means that there is a clinically and statistically significant reduction in the total nasal symptom score from baseline for seasonal allergic rhinitis patients treated with mometasone furoate nasal spray with medium onset to moderate or complete relief at 3 days (35.9 hours) compared to 72 hours for the patients treated with a placebo nasal spray. These results were obtained in a randomized, double-blind, multicenter, placebo-controlled, parallel group study to characterize the period between initiation of dosing with mometasone furoate nasal spray and onset of clinical efficacy as measured by the total nasal symptom score in symptomatic patients with seasonal allergic rhinitis. The study lasted 14 days in length. Data from 201 patients were used for analysis.

A. Clinical Evaluations

1. Seasonal Allergy Rhinitis a. Signs and symptoms were individually scored by the patient on the diary card, and by the investigator or designee at Screening and Baseline (Day 1), Day 4, Day 8, and Day 15 after treatment.

| Signs and Symptoms of Rhinitis | |
|---|---|
| Nasal | Non-Nasal |
| Nasal stuffiness/congestion | Itching/buring eyes |
| Rhinorrhea (nasal discharge/ runny nose) | Tearing/watering eyes |
| | Redness of eyes |
| Nasal itching, | Itching of ears or palate |
| Sneezing | |

All symptoms (nasal and non-nasal) were rated by the investigator or designee according to the following scale:

| 0 = None: | No signs/symptoms are evident |
|---|---|
| 1 = Mild: | Signs/symptoms are clearly present but minimal awareness; easily tolerated |
| 2 = Moderate: | Definite awareness of signs/symptoms which are bothersome but tolerable |
| 3 = Severe: | Signs/symptoms are hard to tolerate; may cause interference with activities of daily living and/or sleeping |

2. Overall Condition of Seasonal Allergic Rhinitis

The overall condition of rhinitis was evaluated by the investigator or designee and patient at the same time as symptoms, and scored according to the following criteria:

| 0 = None: | No signs/symptoms are evident |
|---|---|
| 1 = Mild: | Signs/symptoms are clearly present but minimal awareness; easily tolerated |
| 2 = Moderate: | Definite awareness of signs/symptoms which are bothersome but tolerable |
| 3 = Severe: | Signs/symptoms are hard to tolerate; may cause interference with activities of daily living and/or sleeping. |

In order to qualify for randomization, a patient must have had:

1. Nasal congestion $\geq 2$ (moderate) at both Screening and Baseline.

2. Total score of the four nasal symptoms $\geq 7$ at both Screening and Baseline.

3. Overall condition $\geq 2$ (moderate) at both Screening and Basline.

At visits after Basline, evaluations included the entire time period since the last visit, up to and including the time of the current observations.

3. Drug—Each patient was given a metered nasal pump spray bottle containing either an aqueous suspension of mometasone furoate or placebo. Dosing instructions on the bottle informed patient to deliver 2 sprays of drug (mometasone furoate 50 mcg/spray) or placebo into each nostril once-a-day, each morning.

4. Clinical Efficacy

1. Parameters

After the Baseline visit, each patient was instructed to enter into his/her diary the information about the time of onset of nasal relief and level of nasal symptom relief as no relief, slight, moderate, marked, or complete.

At Baseline and each follow-up visit, the physician evaluated the following signs and symptoms of allergic rhinitis, scored as 0=none, 1=mild, 2=moderate, 3=severe.

a. NASAL SYMPTOMS
   nasal discharge
   congestion/stuffiness
   sneezing
   itching b. TOTAL NASAL SCORE: sum of the 4 individual nasal scores c. COMPOSITE TOTAL SCORE: sum of the 8 nasal and non-nasal scores The overall condition of rhinitis was also evaluated by both the physician and patient using the same scoring system.

At each follow-up visit post Baseline, the physician and patient evaluated the therapeutic response as 5=no relief, 4=slight relief, 3=moderate relief, 2=marked relief, 1=complete relief.

After the Baseline visit, each morning and evening the patient completed a diary to assess the 8 signs and symptoms of allergic rhinitis as described above.

Results

The primary efficacy results are based on a survival analysis of the onset times of relief (defined as the first time patient experienced at least moderate relief of nasal symptoms) for the mometasone furoate nasal spray and placebo groups. In this analysis, patients reporting slight or no relief for the first 3 days after treatment were censored at Day 3. Also, results from the patient regular diary (by 15-day average) data were evaluated.

Data from 201 patients were used in the survival analysis. There were 101 patients in the mometasone furoate nasal spray group and 100 patients in the placebo group. From the individual patient onset diary data, it was found that there were a total of 24 patients who recorded slight or no relief (i.e. censored) at Day 3 in the mometasone furoate nasal spray group as compared to 50 patients in the placebo group similarly recording slight or no relief (i.e. censored).

Survival analysis results suggest that mometasone furoate nasal spray group had a median onset time to relief of 35.9 hours as compared to placebo group's 72 hours (due to more censored observations in this group). From a plot of the survival distribution for the two groups, it was seen that proportion reporting slight or no relief with increasing duration (in total hours) in the placebo group was higher compared to the mometasone furoate nasal spray group. Using a log-rank data showed a statistically significant difference between the two treatment groups ($p$-value<0.001).

Analysis of morning & evening averaged diary data showed that (for the 15-days average) reduction in the total nasal symptom score from baseline for mometasone furoate nasal spray group was statistically significantly higher than that for the placebo group.

In a first Phase I trial of the mometasone furoate dry powder inhaler (DPI), mometasone furoate-DPI was once-a-day given to eight normal volunteers in single doses of 400, 800, 1600, 3200 mcg and placebo. Parallel groups of volunteers received either budesondie dry powder (400, 800, 1600, 3200 mcg and placebo) or prednisone (5 mg, 10 mg, 20 mg, 40 mg, or placebo). All doses were administered at 11 p.m., and plasma cortisol levels over the next 24 hours were monitored.

Drug Metabolism/clinical Pharmacology Study

A drug metabolism and clinical pharmacology study was conducted by administering (by various routes) tritium-labeled mometasone furoate ("$^3$H-MF") to 6 groups of 6 normal male volunteers in each group. Blood and urine samples were collected for measurement of total drug (including metabolites).

The objectives of these studies in male volunteers were to determine the absorption, metabolism and excretion of $^3$H-labeled mometasone furoate ("$^3$H-MF") following administration by oral swallow as a solution and as an aqueous suspension of the monohydrate, by oral inhalation as a suspension from a standard metered dose inhaler (MDI) and from a metered dose inhaler containing a spacer device (Gentlehaler), by nasal inhalation as an aqueous suspension of the mometasone furoate monohydrate from a nasal spray unit and by intravenous injection as a solution.

Population

Thirty-six (n=6 per treatment group) normal healthy male volunteers between the ages of 19 and 40 yr. (average 29 yr.) having weights in accordance with current actuarial tables (+10%) were enrolled in these single dose studies. All subjects were determined to be in good health by their medical history, physical examinations, clinical and laboratory tests.

Study Design

Six volunteers in each of the six treatment groups received one of the following $^3$H-MF dosage forms listed in Table 1:

TABLE 1

| Dosage Form | Dose* mg/Subject | µCi/Subject | Mode of Administration |
|---|---|---|---|
| Oral Solution | 1.03 | 209 | 33.3 ml (0.031 mg/ml) by oral swallow |
| MDI (metered-dose inhaler) | 0.86 | 163 | 4 puffs from a MDI canister (215 µg/actuation) |
| Nasal Spray | 0.19 | 197 | 4 sprays from a nasal spray bottle (47 µg/spray) |
| Gentlehaler | 0.40 | 79 | 4 bursts from a MDI canister containing a spacer (referred to as Gentlehaler) (101 µg/burst) |
| Intravenous Solution | 1.03 | 204 | 1.03 mg/ml administered at a rate of 1 ml/min. |
| Oral Suspension (hydrated) | 0.99 | 195 | 1.6 ml (0.62 mg/ml by oral swallow |

*Doses based on analysis of dosage forms prior to start of study

Plasma, urine, expired air filters, Respirgard and fecal samples were collected and assayed for radioactivity content. The limit of quantitation (LOQ) for plasma radioactivity ranged from 0.103 to 0.138 ng eq/ml., except for the nasal spray treatment where the LOQ was 0.025 ng eq/ml. Selected plasma, urine and fecal samples were analyzed for metabolite profiles.

Results

Clinical Summary—Mometasone furoate was found to be safe and well tolerated by all volunteers after administration of all dosage forms.

Pharmacokinetics—The mean (n=6) plasma concentrations of total radioactivity are illustrated in Summary FIG. 1 and the mean (n=6) pharmacokinetic parameters derived from total plasma radioactivity are presented in Table 2.

Comparison of plasma radioactivity illustrated in FIG. 1 and/or urinary excretion data and presented in Table 2 after the various formulations with those after intravenous treatment demonstrated that drug-derived radioactivity was completely absorbed when $^3$H-MF was administered orally as a solution. In contrast, systemic absorption of drug-derived radioactivity following administration of $^3$H-MF as an oral suspension or as a nasal spray suspension was approximately 8% of the dose. Systemic absorption of drug-derived radioactivity following administration of $^3$H-MF via the MDI (30%) and Gentlehaler™ (67%) was higher than that following nasal spray or oral suspension. Although the peak plasma concentration of radioactivity was less than 1 ng eq/ml for both MDI and Gentlehaler, comparative dose normalized AUC radioactivity data and urinary excretion data suggested that absorption of drug-derived radioactivity from the MDI and Gentlehaler was approximately 23–30% and 67–69%, respectively. The drug derived radioactivity data suggested that systemic bioavailability was greater following administration with the Gentlehaler™ compared to MDI administration. This may have been the result of enhanced lung deposition of drug due to the use of a spacer device in the Gentlehaler™. The Gentlehaler™ device is a MDI actuator described in U.S. Pat. No. 4,972,830.

Radioactivity was predominantly excreted in the feces regardless of dosage form and route of administration. Excretion of radioactivity in the urine was approximately 25% for the intravenous and oral solution formulations, 7% for the MDI and 16% for the Gentlehaler and 2% or less for both the nasal spray and oral suspension formulations, respectively. These data thus demonstrate that the drug was well absorbed when orally administered as a solution formulation but poorly absorbed following oral or intranasal administration as a suspension formulation.

TABLE 2

PHARMACOKINETIC PARAMETERS OF TOTAL RADIOACTIVITY
FOLLOWING ADMINISTRATION OF $^3$H-MF IN MALE VOLUNTEERS

| Parameter | Dosage Form | | | | | |
|---|---|---|---|---|---|---|
| | Intravenous | Oral Solution | MDI | Gentlehaler | Nasal Spray | Oral Suspension |
| Cmax | 23.7 | 4.8 | 0.80 (0.93*) | 0.69 (1.71*) | BQL** | BQL |
| AUC (1) | 401 | 488 | 81 (94*) | 110 (275*) | BQL | BQL |

TABLE 2-continued

| | | | | | | |
|---|---|---|---|---|---|---|
| Urine (% dose) | 24 | 25 | 7 | 16 | 2 | 2 |
| Feces (% dose) | 54 | 62 | 86 | 89 | 78 | 73 |
| U + F (% dose) | 78 | 87 | 94 | 105 | 80 | 75 |
| % Absorbed | | | | | | |
| AUC | — | 122 | 23* | 69* | — | — |
| Urine | — | 104 | 30 | 67 | 8 | 8 |

| Parameter | Units | Definition |
|---|---|---|
| Cmax | ng eq/ml | Maximum plasma concentration, except for the intravenous treatment, which is $C_{5min}$. |
| AUC (1) | ng eq hr/ml | Area under the plasma concentration-time curve to infinity. |
| Urine (% dose) | % | Percent of administered radioactivity excreted in the urine through 168 hr. |
| Feces (% dose) | % | Percent of administered radioactivity excreted in feces through 168 hr. |
| U + F (% dose) | % | Total percent dose recovered in the urine and feces through 168 hr. |
| % Absorbed (AUC) treatment data | % | Percent of administered radioactivity absorbed based on dose normalized versus intravenous data. |
| % Absorbed (Urine) data) | % | Percent of administered radioactivity absorbed (based on urinary excretion compared to the intravenous dose. |

*Based on dose normalized data
**BQL = Below Quantifiable Limit

Selected plasma, urine and fecal extracts were analyzed by high performance liquid chromatography (HPLC) with radio-flow monitoring to determine metabolite profiles. The results of these analyses demonstrated that, following administration of the oral solution, most of the plasma radioactivity was associated with metabolites more polar than the available standards. Approximately 1.5% of the 3 hr. plasma radioactivity was associated with parent drug indicating extensive first past metabolism and rapid inactivation by the the liver. In contrast, following intravenous administration, approximately 39% of the 3 hr. plasma radioactivity was associated with parent drug. Approximately 12% and 33% of the 3 hr. plasma radioactivity was associated with parent drug following administration of the MDI and Gentlehaler, respectively. In general, the plasma concentrations of radioactivity following the nasal and oral suspension routes of administration were too low for metabolite profiling.

HPLC/radio-flow analysis of both urinary and fecal extracts following both intravenous and oral solution administration demonstrated that all of the radioactivity was associated with metabolites more polar than parent drug. Analysis of urine specimens obtained from subjects who received $^3$H-MF by the Gentlehaler also demonstrated that all of the radioactivity was associated with metabolites more polar than parent drug. However, analyses of fecal extracts following administration of the nasal spray, oral suspension and inhalation (MDI and Gentlehaler) formulations, demonstrated the presence primarily of mometasone furoate, presumably due to unabsorbed drug which was swallowed. Hydrolysis of plasma and urine was performed with an enzyme preparation containing both β-glucuronidase and aryl sulfatase. These experiments yielded modest changes in the HPLC metabolite profiles that were consistent with the hydrolytic release of conjugated metabolites.

The percent of dose as tritiated water in the body was estimated from urinary distillation experiments to be approximately 3.7% after intravenous and 2.9% after oral solution dosing.

These findings suggested that less than 4% of the tritium label had exchanged with body water following administration of $^3$H-MF to male volunteers.

The results of these drug metabolism/clinical pharmacology studies demonstrate that:

1. Drug-derived radioactivity was completely absorbed when $^3$H-MF was given orally as a solution to male volunteers. However, the absolute bioavailability of unchanged mometasone furoate was extremely low (less than approximately 1%) due to extensive first pass metabolism.

2. Drug-derived radioactivity was moderately absorbed following oral inhalation of $^3$H-MF by the metered dose inhaler (23–30%) and Gentlehaler™ (67–69%).

3. The absorption of drug-derived radioactivity following administration of $^3$H-MF nasal spray and oral suspension formulations was approximately 8%.

4. The plasma concentrations of unchanged mometasone furoate could not be determined after administration by oral inhalation as a suspension from a MDI or a Gentlehaler, or by nasal inhalation of an aqueous suspension of mometasone furoate monohydrate from a nasal spray unit or by oral swallow of an aqueous suspension of the monohydrate because the plasma concentrations of total radioactivity were too low for metabolite profiling.

5. Mometasone furoate was extensively metabolized following all routes of administration.

As shown in Table 2, $^3$H-MF-derived radioactivity suggests that systemic absorption was greater from an orally swallowed solution (about 100%) than from an orally swallowed suspension or an intranasally inhaled suspension (8%). Mometasone furoate was detectable in plasma by metabolite profiling after administration of the drug by intravenous injection or oral administration as solution dosage forms, but not after administration of the oral or nasal suspensions. Similarly, the excretion of radioactivity in urine after dosing with the solution formulation was greater (25%) than after dosing with the nasal spray or oral suspension (2%). The total recovery or radioactivity in urine and feces was 87% and 75% respectively, with most of the radioactivity being excreted in the feces. After intravenous dosing, the total radioactivity excreted was 78% with 24%, being excreted in the urine and 54% being excreted in the feces.

What is claimed is:

1. A method of treating a corticosteroid-responsive disease of the upper airway passages comprising administering once daily to nasal passages about 400 micrograms of mometasone furoate.

2. The method of claim 1, wherein the mometasone furoate is administered as anhydrous mometasone furoate.

3. The method of claim 1, wherein the mometasone furoate is administered as memetasone furoate monohydrate.

4. The method of claim 1, wherein the mometasone furoate is administered in the form of an aqueous suspension.

5. The method of claim 1, wherein the mometasone furoate is administered in the form of an aqueous suspension of mometasone furoate monohydrate.

6. The method of claim 1, wherein the mometasone furoate is administered in the form of an aqueous suspension of anhydrous mometasone furoate.

7. The method of claim 1, wherein there are administered 400 micrograms of mometasone furoate by applying four times to each nostril about 50 micrograms of mometasone furoate.

8. A method of treating a corticosteroid-responsive disease, comprising administering once daily to nasal passages an aqueous nasal spray comprising mometasone furoate monohydrate, in an amount providing about 200 micrograms of mometasone furoate to each nostril.

9. The method of claim 8, wherein there are administered 400 micrograms of mometasone furoate by applying four times to each nostril about 50 micrograms of mometasone furoate.

* * * * *

UNITED STATES PATENT AND TRADEMARK OFFICE
CERTIFICATE OF CORRECTION

PATENT NO. : 6,956,030 B2
DATED : October 18, 2005
INVENTOR(S) : Sequeira et al.

It is certified that error appears in the above-identified patent and that said Letters Patent is hereby corrected as shown below:

Column 17,
Line 13, insert the word -- mometasone -- in place of "memetasone.".

Signed and Sealed this

Thirteenth Day of December, 2005

JON W. DUDAS
*Director of the United States Patent and Trademark Office*